(12) United States Patent
Schade et al.

(10) Patent No.: US 9,744,280 B2
(45) Date of Patent: Aug. 29, 2017

(54) METHODS FOR LVAD OPERATION DURING COMMUNICATION LOSSES

(71) Applicant: Thoratec Corporation, Pleasanton, CA (US)

(72) Inventors: Christian Schade, Feldmeilen (CH); Andre Siebenhaar, Gipf-Oberfrick (CH)

(73) Assignee: TC1 LLC, St. Paul, MN (US)

( * ) Notice: Subject to any disclaimer, the term of this patent is extended or adjusted under 35 U.S.C. 154(b) by 21 days.

(21) Appl. No.: 14/687,817

(22) Filed: Apr. 15, 2015

(65) Prior Publication Data
US 2015/0290378 A1 Oct. 15, 2015

Related U.S. Application Data

(60) Provisional application No. 61/979,803, filed on Apr. 15, 2014.

(51) Int. Cl.
*A61M 1/12* (2006.01)
*A61M 1/10* (2006.01)

(52) U.S. Cl.
CPC ............ *A61M 1/122* (2014.02); *A61M 1/101* (2013.01); *A61M 1/1086* (2013.01); *A61M 2205/16* (2013.01)

(58) Field of Classification Search
CPC .................................. A61F 2/24; A61M 1/101
USPC .................................................. 623/3.1–3.18
See application file for complete search history.

(56) References Cited

U.S. PATENT DOCUMENTS

| | | |
|---|---|---|
| 5,695,471 A | 12/1997 | Wampler |
| 5,708,346 A | 1/1998 | Schob |
| 5,725,357 A | 3/1998 | Nakazeki et al. |
| 5,735,882 A | 4/1998 | Rottenberg et al. |
| 5,888,242 A | 3/1999 | Antaki et al. |
| 5,947,703 A | 9/1999 | Nojiri et al. |
| 6,053,705 A | 4/2000 | Schob et al. |
| 6,071,093 A | 6/2000 | Hart |
| 6,100,618 A | 8/2000 | Schoeb et al. |
| 6,116,862 A | 9/2000 | Rau et al. |
| 6,146,325 A | 11/2000 | Lewis et al. |

(Continued)

FOREIGN PATENT DOCUMENTS

EP 750921 1/1997

OTHER PUBLICATIONS

U.S. Appl. No. 14/687,824, filed Apr. 15, 2015, Titled: Methods and Systems for Upgrading Ventricle Assist Devices.
(Continued)

*Primary Examiner* — Suzette J Gherbi
(74) *Attorney, Agent, or Firm* — Kilpatrick Townsend & Stockton LLP (57) ABSTRACT

Methods, systems, and devices for an adaptable blood pump are disclosed herein. The blood pump can be part of a mechanical circulatory support system that can include a system controller and the blood pump. The blood pump can include a rotary motor and a control unit that can communicate with the system controller. The blood pump can determine when communication with the system controller is established or has been lost. The blood pump can retrieve one or several back-up parameters when communication with the system controller has been lost, and can operate according to these back-up parameters.

7 Claims, 9 Drawing Sheets

(56) References Cited

U.S. PATENT DOCUMENTS

| | | |
|---|---|---|
| 6,186,665 B1 | 2/2001 | Maher et al. |
| 6,222,290 B1 | 4/2001 | Schob et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,351,048 B1 | 2/2002 | Schob et al. |
| 6,355,998 B1 | 3/2002 | Schob et al. |
| 6,468,041 B2 | 10/2002 | Ozaki |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,626,644 B2 | 9/2003 | Ozaki |
| 6,634,224 B1 | 10/2003 | Schob et al. |
| 6,652,447 B2 | 11/2003 | Benkowski et al. |
| 6,688,861 B2 | 2/2004 | Wampler |
| 6,707,200 B2 | 3/2004 | Carroll et al. |
| 6,817,836 B2 | 11/2004 | Nose et al. |
| 6,879,074 B2 | 4/2005 | Amrhein et al. |
| 6,949,066 B2 | 9/2005 | Bearnson et al. |
| 6,991,595 B2 | 1/2006 | Burke et al. |
| 7,112,903 B1 | 9/2006 | Schob |
| 7,138,776 B1 | 11/2006 | Gauthier et al. |
| 7,150,711 B2 | 12/2006 | Nüsser et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,591,777 B2 | 9/2009 | LaRose et al. |
| 7,645,225 B2 | 1/2010 | Medvedev et al. |
| 7,699,586 B2 | 4/2010 | LaRose et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,951,062 B2 | 5/2011 | Morello |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,157,720 B2 | 4/2012 | Marseille et al. |
| 8,303,482 B2 | 11/2012 | Schima et al. |
| 8,323,174 B2 | 12/2012 | Jeevanandam et al. |
| 8,382,830 B2 | 2/2013 | Maher et al. |
| 8,449,444 B2 | 5/2013 | Poirier |
| 8,506,470 B2 | 8/2013 | LaRose et al. |
| 8,506,471 B2 | 8/2013 | Bourque |
| 8,517,699 B2 | 8/2013 | Horvath |
| 8,551,070 B2 | 10/2013 | Miller et al. |
| 8,556,795 B2 | 10/2013 | Bolyard et al. |
| 8,562,508 B2 | 10/2013 | Dague et al. |
| 8,597,350 B2 | 12/2013 | Rudser et al. |
| 8,628,460 B2 | 1/2014 | Batty, Jr. et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,764,621 B2 | 7/2014 | Badstibner et al. |
| 8,870,739 B2 | 10/2014 | LaRose et al. |
| 8,882,477 B2 | 11/2014 | Fritz, IV et al. |
| 8,956,275 B2 | 2/2015 | Bolyard et al. |
| 2003/0069465 A1 | 4/2003 | Benkowski et al. |
| 2005/0071001 A1 | 3/2005 | Jarvik |
| 2007/0078293 A1 | 4/2007 | Shambaugh, Jr. et al. |
| 2007/0142696 A1 | 6/2007 | Crosby et al. |
| 2008/0021394 A1 | 1/2008 | LaRose et al. |
| 2009/0203957 A1 | 8/2009 | LaRose et al. |
| 2010/0130809 A1 | 5/2010 | Morello |
| 2010/0152526 A1* | 6/2010 | Pacella ............... A61M 1/101 600/17 |
| 2010/0241223 A1 | 9/2010 | Lee et al. |
| 2010/0327687 A1 | 12/2010 | Iannello et al. |
| 2011/0066211 A1 | 3/2011 | Von Arx et al. |
| 2011/0071337 A1 | 3/2011 | Thompson et al. |
| 2011/0160518 A1* | 6/2011 | Zafirelis ............... A61M 1/101 600/16 |
| 2011/0237863 A1 | 9/2011 | Ricci et al. |
| 2011/0313237 A1 | 12/2011 | Miyakoshi et al. |
| 2012/0022645 A1 | 1/2012 | Burke et al. |
| 2012/0046514 A1 | 2/2012 | Bourque |
| 2012/0095281 A1 | 4/2012 | Reichenbach et al. |
| 2012/0226097 A1 | 9/2012 | Smith et al. |
| 2012/0245681 A1 | 9/2012 | Casas et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2013/0331934 A1 | 12/2013 | Kabir et al. |
| 2013/0338559 A1* | 12/2013 | Franano ............... A61M 1/101 604/4.01 |
| 2013/0345804 A1 | 12/2013 | Kanebako et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0296615 A1* | 10/2014 | Franano ............... A61M 1/101 600/17 |
| 2014/0303426 A1 | 10/2014 | Kerkhoffs et al. |
| 2014/0357937 A1 | 12/2014 | Reyes et al. |
| 2015/0051438 A1 | 2/2015 | Taskin |
| 2015/0209498 A1* | 7/2015 | Franano ............... A61M 1/3653 600/16 |
| 2015/0290376 A1* | 10/2015 | Schade ............... G06F 19/3412 600/16 |
| 2016/0220748 A1* | 8/2016 | Pouchoulin ......... A61M 1/3621 |
| 2016/0228631 A1* | 8/2016 | Crnkovich ............... G01L 7/088 |
| 2016/0271317 A1* | 9/2016 | Roger ............... A61M 1/3653 |

OTHER PUBLICATIONS

PCT/US2015/026027, "International Search Report and Written Opinion", Jul. 10, 2015, 14 pages.

\* cited by examiner

METHODS FOR LVAD OPERATION DURING COMMUNICATION LOSSES

CROSS-REFERENCES TO RELATED APPLICATIONS

This application claims the benefit of U.S. Provisional Application No. 61/979,803, filed on Apr. 15, 2014, and entitled "METHODS AND SYSTEMS FOR LVAD OPERATION DURING COMMUNICATION LOSSES," the entirety of which is hereby incorporated by reference herein.

BACKGROUND OF THE INVENTION

This application relates generally to mechanical circulatory support systems, and more specifically relates to control systems, for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

As VAD systems continue to develop and are more widely used, the importance of reliability continues to increase. Reliability become particularly significant in light of the mechanical and electrical complexity of the VAD, and the interrelation and communication between the different components working with the VAD. Thus, new methods, systems, and devices that will increase the reliability of the VAD are desired.

BRIEF SUMMARY OF THE INVENTION

The present invention provides new systems, methods, and devices which can advantageously allow for uninterrupted operation of pump components of the VAD without the receipt of external control signals during a communication loss or interruption. For example, the pump components of the VAD can be separately located from a portion of the system controls of the VAD. This can advantageously increase the implantability of the pump components by decreasing the size of the housing containing the pump components. When the pump components of the VAD are separately housed from a portion of the system controls, the pump components of the VAD can receive control signals from the system controls that direct the operation of the pump components. In the event that these control signals are not received, the pump components of the VAD can operate according to one or several back-up parameters. This is clearly advantageous from the patient's perspective as this decreases the risk of a failure of the VAD due to, for example, interference with communications or a failure of the system controls. Thus, this capability increases the robustness and reliability of the VAD and in turn increases patient safety and clinical effectiveness.

One aspect of the present disclosure relates to a mechanical circulatory support system. The mechanical circulatory support system includes a controller that can generate control signals including at least one performance parameter and that can repeatingly transmit the control signals within consecutive time periods, and an implantable blood pump communicatively coupled to the controller. The blood pump can include a rotary motor and a control unit communicatively coupled with the rotary motor. The control unit can track the consecutive time periods, receive the control signals from the controller, and retrieve at least one back-up parameter if a control signal is not received from the controller within a predetermined time period or within a number of the consecutive time periods. In some embodiments, this can ensure operation of the implantable blood pump during a communication interruption or loss.

In some embodiments of the mechanical circulatory support system, the control unit can control at least one of the motion and position of the rotary motor, and specifically, the control unit can control at least one of the speed, mode, or pulse parameter of the motor according to the received control signals or the at least one back-up parameter. In some embodiments, the control unit can determine a current pump performance, compare the current pump performance to the at least one back-up parameter, and generate one or several control signals to achieve the pump performance specified by the at least one back-up parameter. In some embodiments, the predetermined time period can be at least 5 seconds. In some embodiments, one of the consecutive time periods can have a length of time of less than 1 second. In some embodiments, the predetermined number can be at least five consecutive time periods.

In some embodiments of the mechanical circulatory support system, the at least one performance parameter can include at least one of a pump speed, a pump operational mode, and a pulse parameter. In some embodiments, the pulse parameter can be one of a pulse duration, a systolic pressure, a diastolic pressure, and a pulse pressure. In some embodiments, the pump operational mode can be at least one of continuous flow, pulsatile pumping, or non-pulsatile mode. In some embodiments, the at least one back-up parameter can be at least one of a pump speed, pump operational mode, and a pulse parameter, and in some embodiments, the control unit can generate the at least one back-up parameter from the control signal received from the controller. In some embodiments, the control unit can include memory which can store the at least one back up parameter.

In some embodiments of the mechanical circulatory support system, the control unit can return to operation based on control signals received from the external controller when communication is re-established. In some embodiments, the controller can include an external or implantable controller configured to wirelessly transmit the control signals. In some embodiments, the controller can include an external or implantable controller having a driveline coupled to the implantable pump to transmit the control signals. In some embodiments, the control unit can control the mode of the rotary motor according to the received control signals or the at least one back-up parameter, and in some embodiments, the control unit can control the pulse parameter of the rotary motor according to the received control signals or the at least one back-up parameter.

One aspect of the present disclosure relates to an implantable blood pump. The implantable blood pump can include a rotary motor, and a control unit communicatively coupled with the rotary motor. The control unit can repeatedly receive control signals that can include at least one performance parameter, track receipt of the control signals over a time period, and retrieve at least one back-up parameter if a control signal is not received within a predetermined time period to ensure operation of the implantable blood pump during a communication interruption or loss.

In some embodiments of the implantable blood pump, the control unit can provide a status update in response to a received control signal. In some embodiments, the at least one back-up parameter is retrieved if a control signal is not received within the predetermined time period of five seconds. In some embodiments, the at least one performance parameter can include at least one of a pump speed, a pump operational mode, and a pulse parameter. In some embodiments, the pulse parameter can be one of a pulse duration, a systolic pressure, a diastolic pressure, and a pulse pressure, and in some embodiments, the pump operational mode can include at least one of continuous flow, pulsatile pumping, or non-pulsatile mode.

In some embodiments of the implantable blood pump, the at least one back-up parameter can include at least one of a pump speed, a pump operational mode, and a pulse parameter. In some embodiments, the control unit can return to operation based on control signals received from the controller when a new control signal is received. In some embodiments, the rotary motor can be located within a first implantable housing and the control unit can be located in a second implantable housing.

One aspect of the present disclosure relates to a method of operating an implantable blood pump. The method includes repeatedly receiving a control signal that includes at least one blood pump performance parameter, operating the blood pump according to the control signal, triggering a threshold indicating absence of receipt of a new control signal, retrieving at least one back-up parameter that includes a blood pump performance parameter, and operating the blood pump according to the at least one back-up parameter.

In some embodiments of the method, the at least one back-up parameter can be retrieved from memory located on the blood pump. In some embodiments, the threshold can be triggered when a new control signal is not received within a predetermined time period. In some embodiments, the predetermined time period can be at least 5 seconds. In some embodiments, the blood pump performance parameter can include a first portion specifying a pump speed, and a second portion specifying a pulse parameter. In some embodiments, the method includes storing the first portion of the control signal as the at least one back-up parameter. In some embodiments, the method includes receiving a second control signal when the blood pump is operating according to the at least one back-up parameter, and operating the blood pump according to the second control signal.

DETAILED DESCRIPTION OF THE INVENTION

Figure 1:
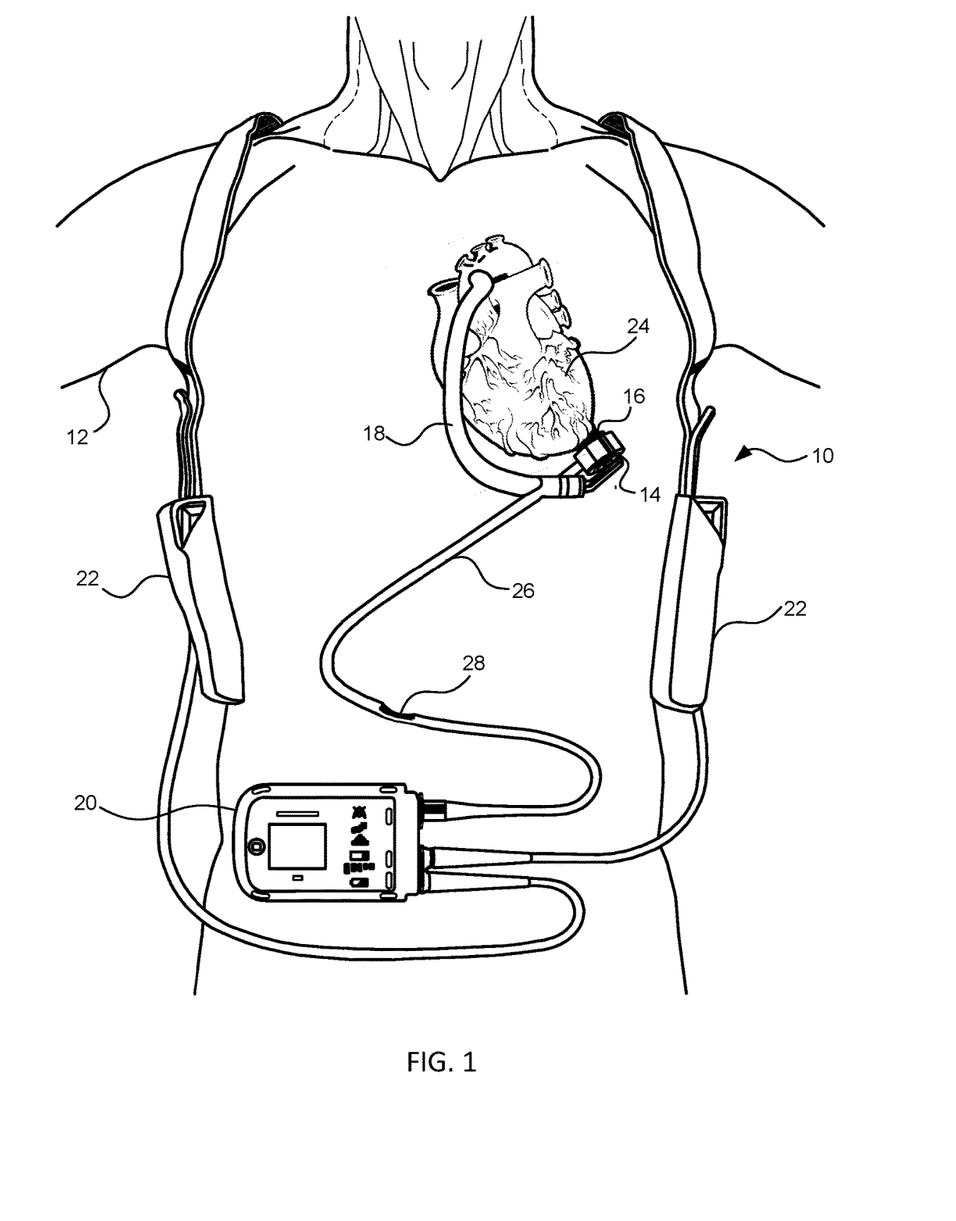
FIG. 1 is an illustration of a mechanical circulatory support system implanted in a patient's body.
Figure 2:
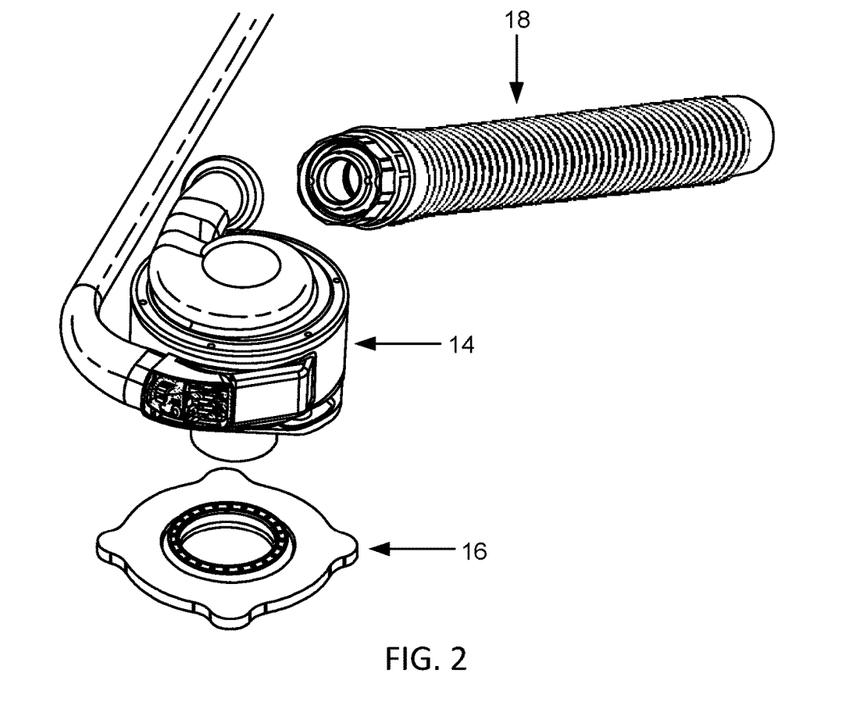
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 3:
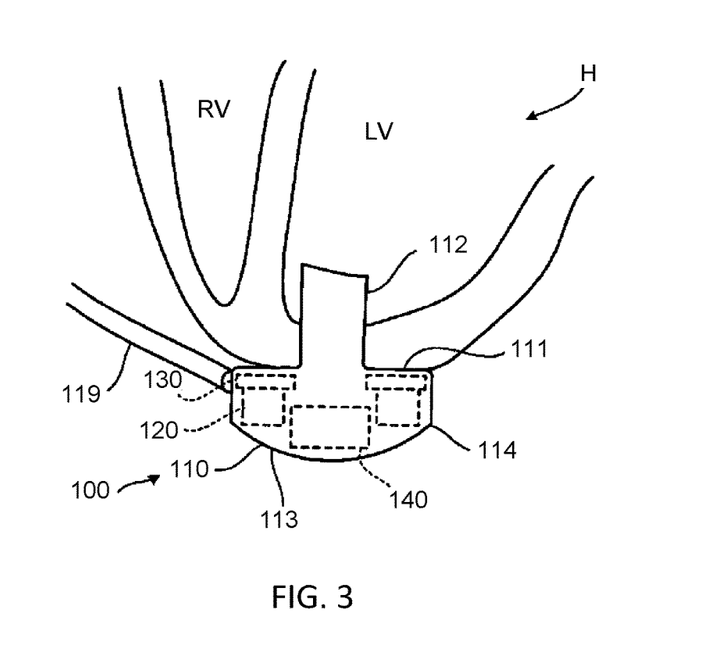
FIG. 3 is an illustration of a blood pump in an operational position implanted in a patient's body.
Figure 4:
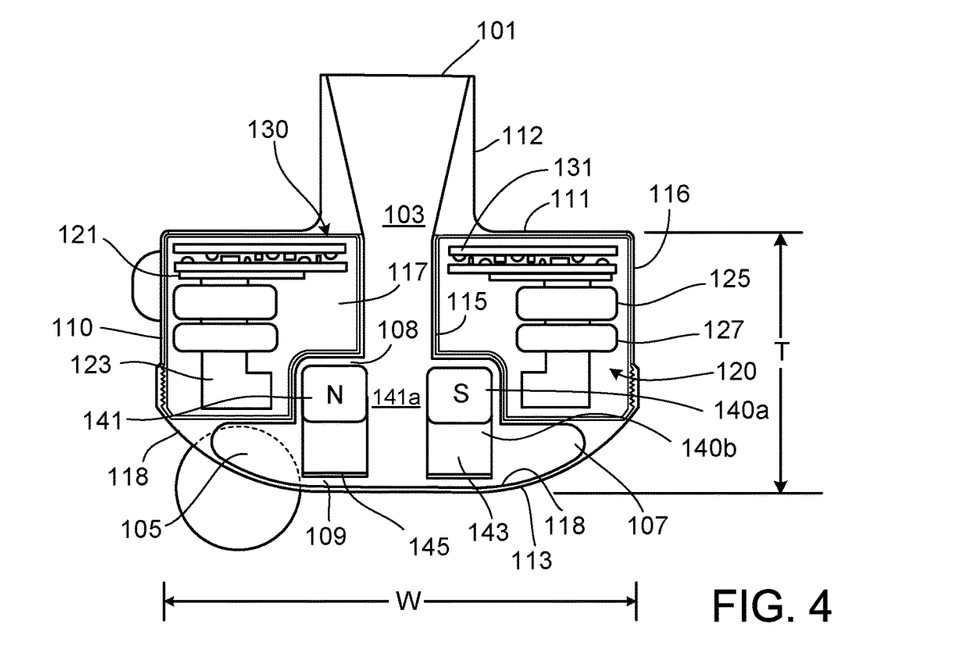
FIG. 4 is a cross-sectional view of the blood pump of FIG. 3.
Figure 5:
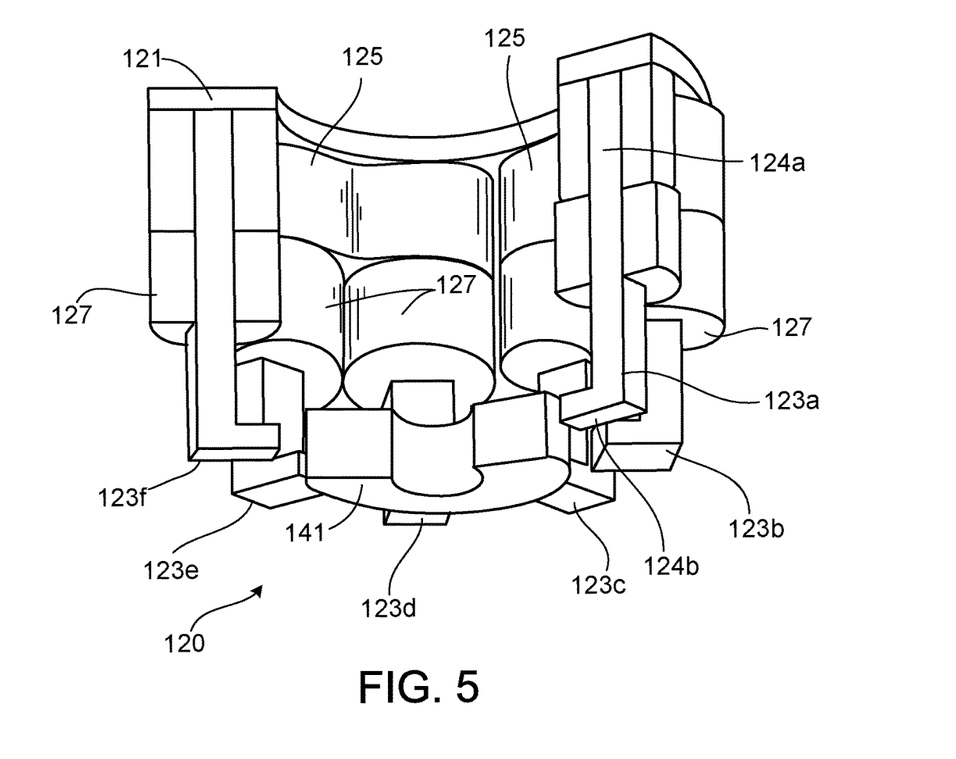
FIG. 5 is a partial cut-away perspective view of a stator of a blood pump.

With reference to FIGS. 3 to 5, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are required proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
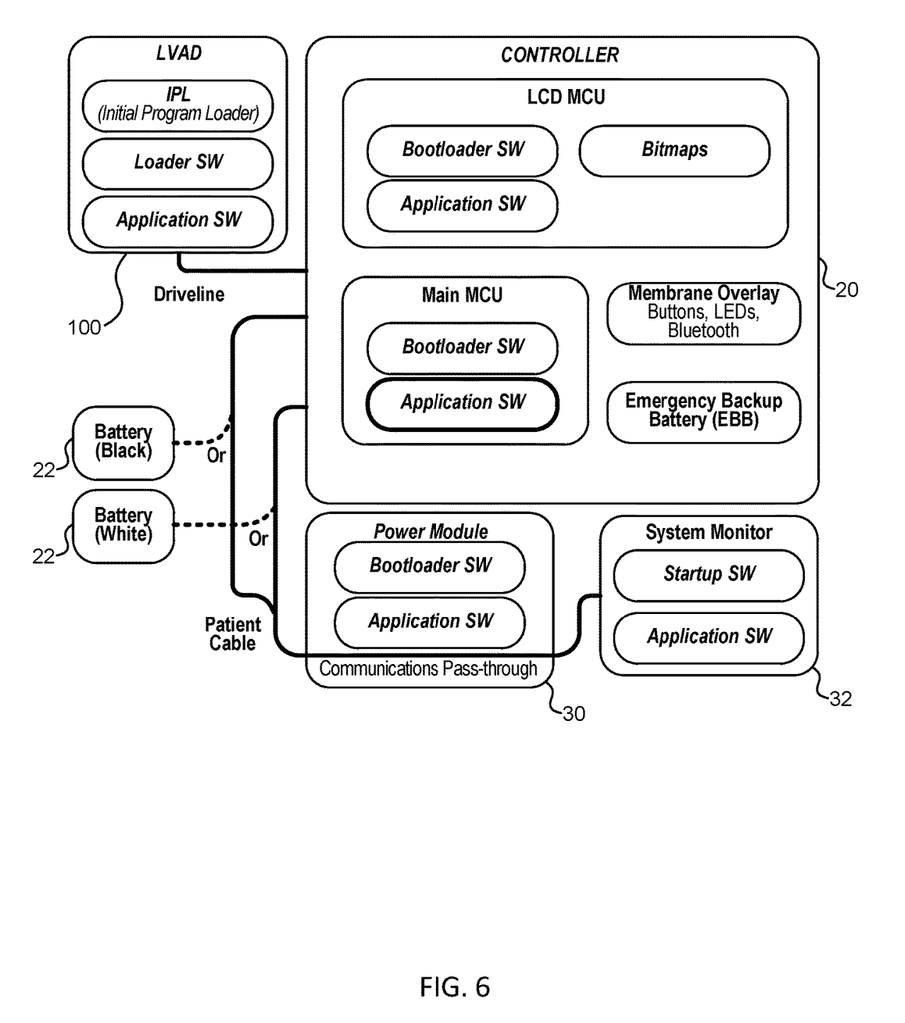
FIG. 6 is a schematic diagram of an overall communication architecture of the mechanical support system of FIG. 1.

FIG. 6 is a schematic diagram of an overall communication architecture of the mechanical support system of FIG. 1. A driveline couples the implanted blood pump 100 to the system controller 20, which monitors system operation via various software applications. The blood pump 100 itself also includes several software applications that are executable by the on board electronics 130 (e.g., processors) for various functions, such as to control radial levitation and/or drive of the rotor of the pump 100 during operation. The system controller 20 may in turn be coupled to batteries 22 or a power module 30 that connect to an AC electrical outlet. The system controller 20 may also include an emergency backup battery (EBB) to power the system (e.g., when the batteries 22 are depleted) and a membrane overlay, including bluetooth capabilities for wireless data communication. An external computer having a system monitor 32 that is configurable by an operator, such as clinician or patient, may further be coupled to the circulatory support system for configuring the system controller 20, implanted blood pump 100, and/or patient parameters, updating software on the system controller 20 and/or implanted blood pump 100, monitoring system operation, and/or as a conduit for system inputs or outputs.

In some embodiments, the software applications of the blood pump 100 can include, for example, an initial program loader (IPL), loader software, and/or application software. In some embodiments, the IPL can be configured to select and load one or several software applications corresponding to one or several modes of operation of the blood pump 100. In some embodiments, these one or several modes of operation of the blood pump 100 can include an operation mode, a test mode, a fault mode, or the like. The selecting and loading of one or several software applications corresponding to one or several modes of operation of the blood pump 100 can include, for example, selecting and loading one or several of the loader software and/or the application software. In some embodiments, the IPL can include information relating to one or several failsafe and/or fault protocols that can be used by the blood pump 100. Some of these failsafe and/or fault protocols will be discussed at length below.

The loader software, can, in some embodiments, be configured to direct the operation of the blood pump 100 during the loading of one or several software applications onto the blood pump 100. These one or several software applications can include, for example, one or several application softwares, one or several IPL applications, or the like. In some embodiments, the loader software can prescribe one or several processes for updating and/or loading one or several software applications onto the blood pump 100. These processes and associated failsafes will be discussed in greater details below.

The application software can include one or several parameters for directing the pumping operation of the blood pump 100. In some embodiments, the application software can comprise one of a clinical application software which can be configured to control the operation of the blood pump 100 when implanted in a patient, and in some embodiments, the application software can comprise a production software that can be configured to control the operation of the blood pump 100 during production and/or testing of the blood pump 100.

In some embodiments, these parameters can specify a control or control regimen for the position and/or motion of the rotor 140. For example, these parameters can specify the aspects of the levitation control and/or rotation control of the rotor 140.

In some embodiments, the parameters of the application software can specify, for example a desired performance of the blood pump 100 and/or one or several desired performance parameters, such as, for example, a desired pump speed, and desired pumped flow rate, a pulse generation, or the like. In some embodiments, these parameters can be actively used to control the operation of the blood pump 100, and in some embodiments these parameters can be stored during normal operation of the blood pump 100 and used as part of one or several failsafe and/or fault protocols. In some embodiments, the parameters of the application software can specify the generation and/or collection of data from the blood pump 100 and/or interfacing of the blood pump 100 to other components of the mechanical circulatory support system 10.

In some embodiments, the application software can comprises a first application software containing parameters relating to the current operation of the blood pump, and in some embodiments, the application software can comprise a second application software containing parameters unrelated to the current operation of the blood pump 100. In one embodiment, for example, the blood pump 100 can comprise the second application software as a backup to the first application software. In some embodiments, the first application software can be identical to the second application software, and in some embodiments, the first application can be different than the second application software.

Figure 7:
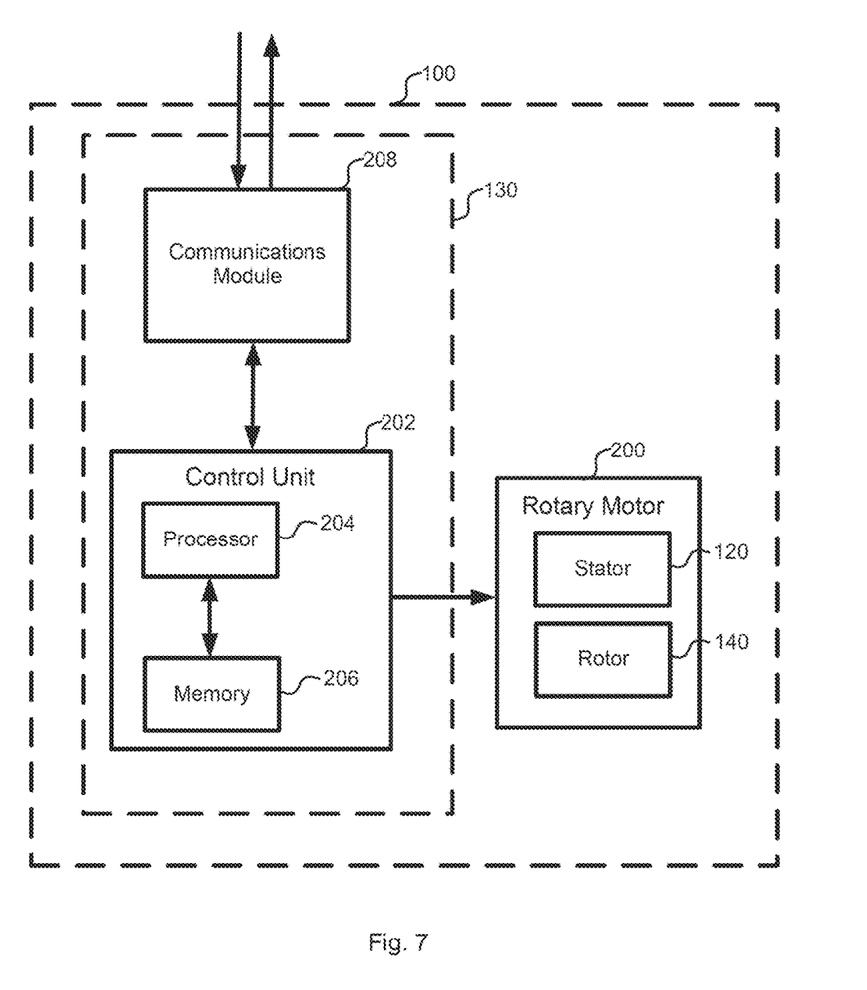
FIG. 7 is a schematic diagram illustrating one embodiment of a blood pump.

FIG. 7 is a schematic diagram illustrating one embodiment of the blood pump 100. As seen in FIG. 7, the blood pump 100 includes electronics 130 and a rotary motor 200, which rotary motor 200 can include the stator 120 and the rotor 140. As seen in FIG. 7, the electronics 130 can include a control unit 202 that can control the operations of the blood pump 100 and can interact with other components of the mechanical circulatory support system 10. As shown, the control unit 202 can communicate with the rotary motor 200 and with the communications module 208. In some embodiments, the control unit 202 and electronics 130 can be located in the same implantable housing 110 as the rotary motor 200, and in some embodiments, the control unit and electronics can be located in a separate implantable housing than the blood pump housing 110. For example, the system controller 20 can be located in an implantable housing, and the control unit 202 and electronics 130 can be co-located in that same implantable housing in a fully implantable transcutaneous energy transfer system.

The control unit 202 can include a processor 204. The processor 204 can provide instructions to, and receive information from the other components of the blood pump 100 and/or from the other components of the mechanical circulatory support system 10. The processor 204 can act according to stored instructions, which stored instructions can be located in memory 206 associated with the processor 204 and/or in other components of the blood pump 100 and/or of the mechanical circulatory support system 10. The processor 204 can comprise a microprocessor, such as a microprocessor from Intel® or Advanced Micro Devices, Inc.®, or the like.

In some embodiments, the stored instructions directing the operation of the processor 204 may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

As seen in FIG. 7, the control unit 202 includes a memory 206. In this embodiment, the memory 206 is the storage medium containing the stored instructions. The memory 206 may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory 206 may be implemented within the processor 204 or external to the processor 204. In some embodiments, the memory 206 can be any type of long term, short term, volatile, nonvolatile, or other storage medium and is not to be limited to any particular type of memory or number of memories, or type of media upon which memory is stored. In some embodiments, the memory 206 can include, for example, one or both of volatile and nonvolatile memory. In one specific embodiment, the memory 206 can include a volatile portion such as RAM memory, and a nonvolatile portion such as flash memory.

In some embodiments, the memory 206 can be divided into one or several partitions. In one embodiment in which the memory 206 contains a plurality of software applications, the memory 206 can be divided into a plurality of partitions so as to be, for example, in a one to one relationship with the number of software applications in the plurality of software applications. In some embodiments, some or all of the software applications stored in the memory 206 can be stored in a unique one of the partitions in the memory 206. In one embodiment in which the memory 206 comprises a volatile portion and a nonvolatile portion, the partitions can be created in one or both of the volatile portion and the nonvolatile portion. Specifically, in one embodiment in which the memory 206 comprises RAM and flash memory, the flash memory can be divided into a plurality of partitions. In some embodiments, the plurality of software applications can be stored in the plurality of partitions in the flash memory.

As described above, the processor 204 can send information and/or signals with and/or receive information and/or signals from the communications module 208. The communications module 208 can include features configured to send and receive information, including, for example, an antenna, a transmitter, receiver, or any other feature that can send and receive information. The communications module 208 can communicate via a wired or wireless link with, for example, the system controller 20 and/or the rotary motor 200. In some embodiments, the communications module 208 can communicate via cellular networks, WLAN networks, or any other wireless network. In some embodiments, the blood pump 100 can be configured to generate a signal in response to some or all communications received from the system controller 20, and/or to not generate a signal to the system controller 20 unless a signal from the system controller 20 has been first received by the blood pump 100.

Figure 8:
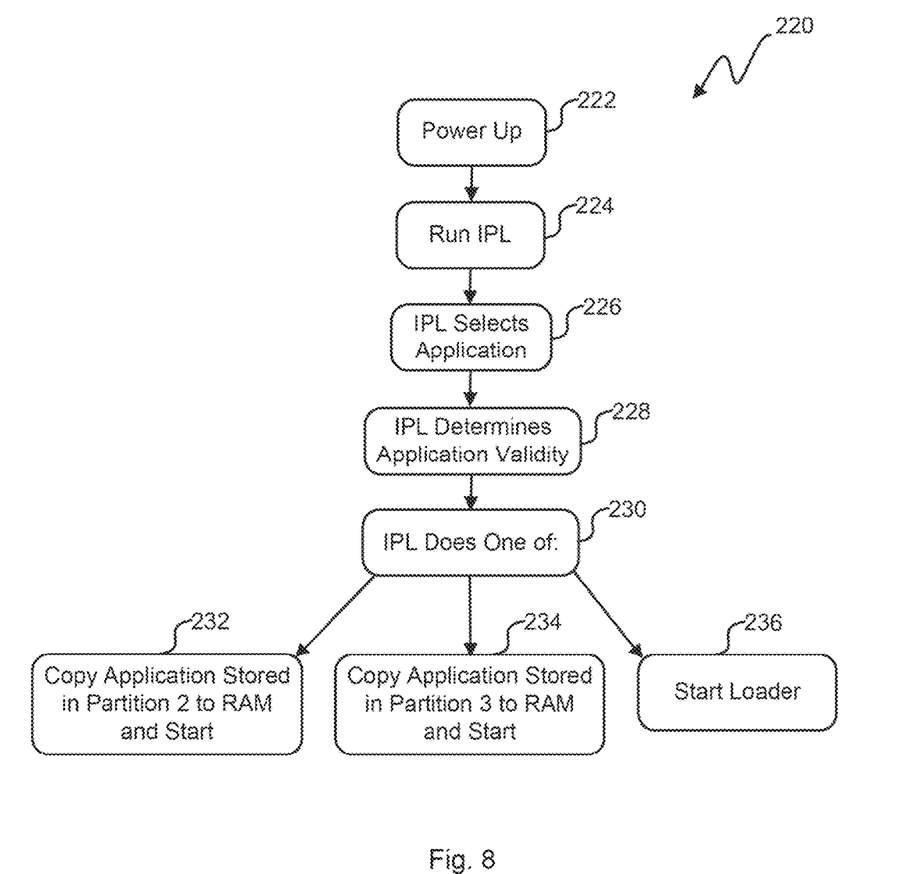
FIG. 8 is a flowchart illustrating one embodiment of operation of the blood pump.

FIG. 8 is a flow-chart illustrating one embodiment of a process 220 for operation of the blood pump 100. The process 220 can be performed to start the pumping of the blood pump 100, and can be performed using components of the blood pump 100 including, for example, the control unit 202. The process 220 begins, in some embodiments, at block 222 wherein the blood pump 100 is powered up. In some embodiments, the powering up the blood pumped 100 can include the receipt of power by the blood pump 100 from one of the batteries 22 and/or other power source. In some embodiments, after the blood pump 100 is powered, the process 220 proceeds to block 224 wherein the IPL is run. In some embodiments, the running of the IPL can include, for example, retrieval of the IPL from the memory 206 and the execution of IPL instructions by the processor 204.

After the IPL is running, the process 220 proceeds to block 226 wherein the IPL selects one or several software applications for control of the blood pump 100. In some embodiments, the one or several software applications can be selected from the memory 206. After the one or several software applications have been selected, the process 220 proceeds to block 228 wherein the IPL determines the validity of the one or several selected software applications. In some embodiments, this can include the determination of the functionality of the one or several software applications and/or the detection of any faults and/or errors in, or caused by the one or several selected software applications.

After the IPL has determined the validity of the one or several selected software applications, the process 220 proceeds to block 230 wherein the IPL retrieves the one or several selected software applications from the memory 206 and starts the one or several selected software applications. As specifically seen in FIG. 8, the IPL can, for example, and as depicted in block 232, copy a software application stored in one of the partitions of the memory 206, such as, for example, a second partition in the flash memory, to the RAM and start the copied software application. Similarly, in one embodiment, the IPL can, and as depicted in block 234, copy a software application stored in one of the partitions of the memory, such as, for example, a third partition in the flash memory, to the RAM and start the copied software application. In some embodiments, the starting of the software application stored in one of the second partition and the third partition can result in the starting of the blood pump 100, the starting of the movement of the rotor 140, and the starting of the associated pumping of blood. In one embodiment, the IPL can, as depicted in block 236, start the loader software. In some embodiments, the loader software can be started as an early step in the update of the blood pump 100.

Figure 9:
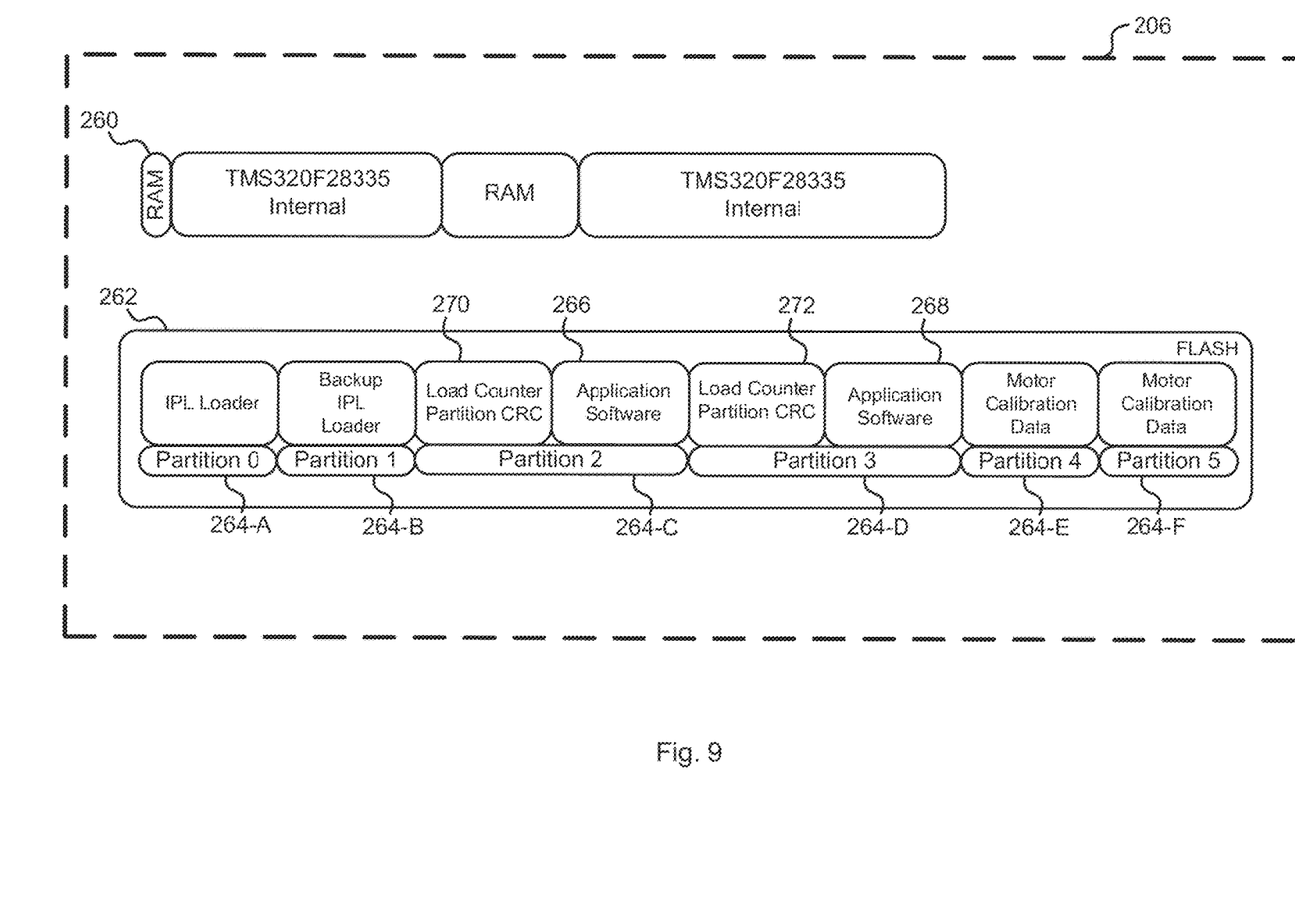
FIG. 9 is a schematic illustration of some of the operations of the blood pump.

FIG. 9 is a schematic illustration of one embodiment of memory 206 of the blood pump 100. As depicted in FIG. 9, the memory 206 of the blood pump can include volatile memory, such as RAM 260 and non-volatile memory such as flash 262. The flash 262 can be divided into several partitions. In the embodiment depicted in FIG. 9, the flash 262 is divided into partition 0 264-A, partition 1 264-B, partition 2 264-C, partition 3 264-D, partition 4 264-E, and partition 5 264-F. As seen in FIG. 9, some of the partitions 264-A-264-F contain a software application. Specifically, partition 0 264-A contains the IPL and loader software, partition 1 264-B contains a backup copy of the IPL and loader software, and partition 2 264-C and partition 3 264-D each contain application software and application software information. In some embodiments, partition 2 264-C and partition 3 264-D correspond to the second and third memory partitions, respectively.

In some embodiments, and as seen in FIG. 9, partition 2 264-C and partition 3 264-D are each divided into first and second portions. In the embodiment depicted in FIG. 9, the first portion of partition 2 264-C contains first application software 266 and the first portion of partition 3 264-D contains second application software 268. In the embodiment depicted in FIG. 9, the second portion of partition 2 264-C contains first application software information 270 and the second portion of partition 3 264-D contains second application software information 272. In some embodiments, the application software information can include, a datum that can be used to identify/verify the application software, such as, for example, a hash or a checksum and information either absolutely or relatively identifying the time and/or date that the application software was loaded on the blood pump 100.

Figure 10:
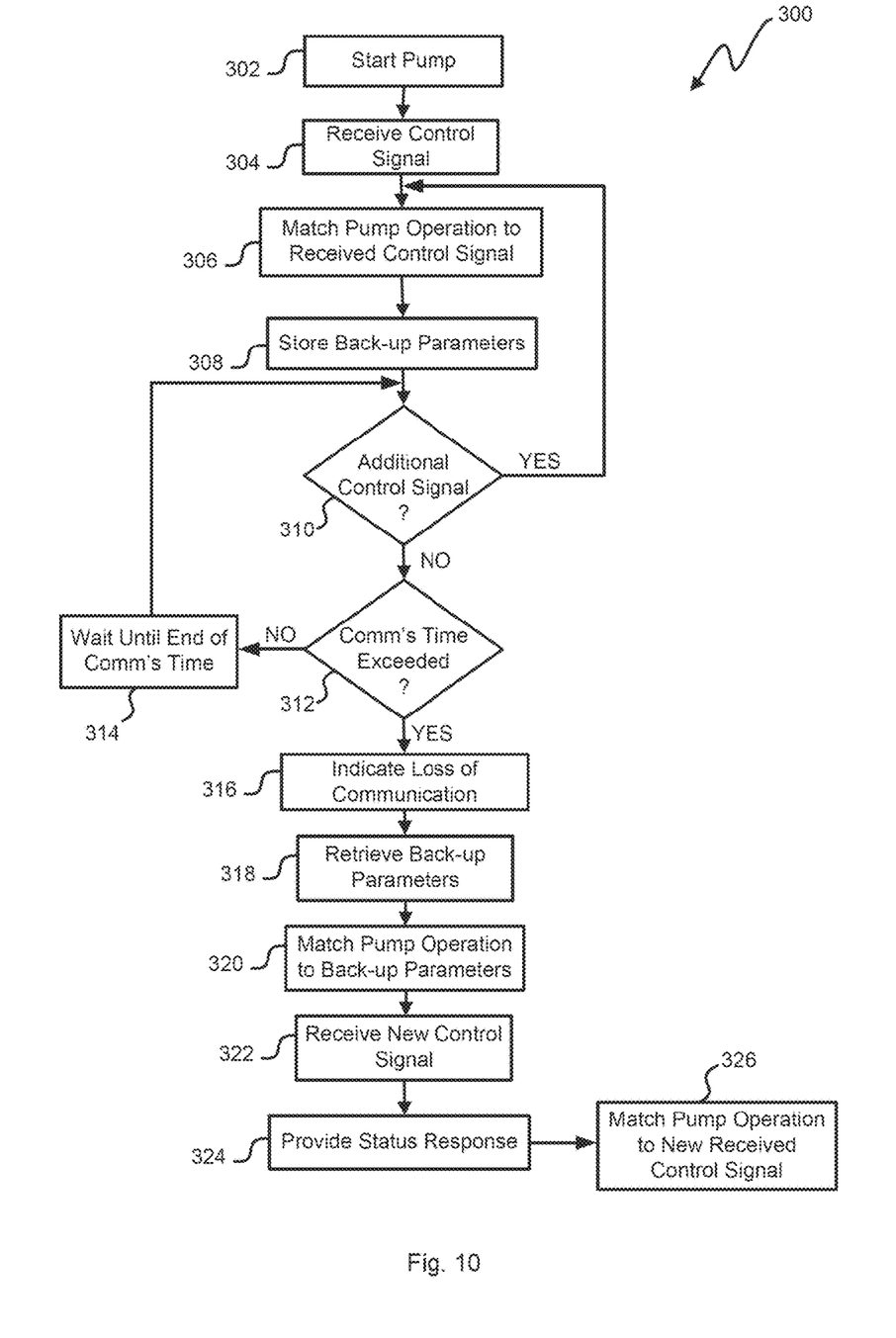
FIG. 10 is a flowchart illustrating one embodiment of a process for operation of the blood pump when communication with a system controller is lost.

FIG. 10 is a flowchart illustrating one embodiment of a process 300 for operation of the blood pump 100 when communication with the system controller 20 is lost or interrupted. In some embodiments, the process 300 can be performed on the blood pump 100 and/or by components communicatively coupled to the blood pump 100 such as, for example, the electronics 130 and/or the control unit 202. The process 300 begins at block 302 wherein the blood pump 100 is started, and specifically, wherein the pumping of the blood pump 100 is initiated. In some embodiments, the blood pump 100 can be started according to the process 220 shown in FIG. 8.

After the blood pump 100 has been started, the process 300 proceeds to block 304, wherein a control signal is received from the system controller 20. In some embodiments, the control signal received from the system controller 20 can be used by the control unit 202 in the controlling of the position, motion, and/or performance of the rotor 140 of the blood pump 100. The control signal can be received by the control unit 202 of the blood pump 100, and specifically, in some embodiments, can be received by the communications module 208 of the blood pump 100.

After the control signal has been received, the process 300 proceeds to block 306, wherein the blood pump operation/performance is matched to the operation/performance specified by the control signal. In some embodiments, this can include determining the current operation/performance of the blood pump 100, comparing the current operation/performance of the blood pump 100 to the operation/performance specified by the control signal, and controlling components of the stator 120 to achieve the operation/performance specified by the control signal if the current operation/performance of the blood pump 100 differs from the operation/performance specified by the control signal. In some embodiments, the matching of the pump operation/performance to the operation/performance specified in the control signal can further include the generation and transmission of a message by the control unit 202 to the system controller 20, which message can identify the current operation/performance of the blood pump 100.

After the blood pump operation/performance has been matched to the operation/performance specified by the control signal, the process 300 proceeds to block 308, wherein at least one back-up parameter is stored. In some embodiments, the back-up parameters can include one or several back-up parameters, and can be stored in the memory 206 of the blood pump 100. Specifically, in some embodiments, the back-up parameters can be stored in one of the partitions 264-A-264-F of the flash memory. In some embodiments, the one or several back-up parameters can be received as a component of the control signal, in some embodiments, the one or several back-up parameters can be created from data received from the control signal, and in some embodiments, the one or several back-up parameters can be received separate from the receipt of the control signal. The details of the creation of the one or several back-up parameters will be discussed at greater length below.

After the one or several back-up parameters have been stored, the process 300 proceeds to decision state 310, wherein it is determined if additional control signals and/or communications from the system controller 20 have been received. In some embodiments, this can include receiving information from, for example, the communications module 208 relating to any received communications. If an additional communication and/or control signal has been received, then the process 300 returns to block 306 and proceeds as outlined above.

If no additional control signal and/or communication has been received, then the process 300 proceeds to decision state 312, wherein it is determined if the communication time has been exceeded. In some embodiments, the communication time can be, for example, an anticipated and/or desired frequency with which communications are expected from the system controller 20. In one embodiment, for example, the communication time can indicate that a communication is expected from the system controller 20 every ten seconds, every five seconds, every second, twice a second, five times a second, ten times a second, and/or at any other or intermediate frequency.

In some embodiments, the communication time can be the maximum length of time that can pass without receiving a communication from the system controller 20 before an error is identified and/or an alarm is triggered. In one embodiment, for example, this amount of time can be one minute, thirty seconds, ten seconds, five seconds, one second, 0.5 seconds, or any other or intermediate length of time.

In some embodiments, the properties of the communication time can be identified in communication time information stored in, for example, the memory 206 of the blood pump 100. In some embodiments, the communication time information is retrieved from the memory, the length of time that has passed since the last received communication is determined, and the determined length of time that has passed since the last received communication is compared to the communication time. If the length of time that has passed since the last received communication is less than the communication time, then the process 300 proceeds to block 314 and waits until the end of the communication time. In some embodiments, the process 300 then proceeds to decision state 310 and proceeds as outlined above.

If it is determined that the communication time has been exceeded, then the process 300 proceeds to block 316, wherein the loss or interruption of communication is indicated. In some embodiments, the loss of communication can be indicated by triggering an error and/or an alarm. In some embodiments, the loss of communication can be indicated by a value associated with the triggered error and/or alarm, and/or associated with the loss of communication. This value can be stored in the memory 206, and in some embodiments, this value can be stored in the RAM.

After the loss of communication has been indicated, the process 300 proceeds to block 318, wherein one or several back-up parameters are retrieved. In some embodiments, the one or several back-up parameters can contain some or all of the parameters contained in the control signals received from the system controller 20 and that relate to the performance of the blood pump 100 including, for example, the speed, operational mode, or pulse parameter of the rotary motor 200. In some embodiments, the one or several back-up parameters can be retrieved from the memory 206 such as, for example, the flash memory.

After the one or several back-up parameters have been retrieved, the process 300 proceeds to block 320, wherein the wherein the blood pump operation/performance is matched to the operation/performance specified by the one or several back-up parameters. In some embodiments, this can include determining the current operation/performance of the blood pump 100, comparing the current operation/ performance of the blood pump 100 to the operation/performance specified by the one or several back-up parameters, and controlling components of the stator 120 to achieve the operation/performance specified by the one or several back-up parameters, if the current operation/performance of the blood pump 100 differs from the operation/performance specified by the one or several back-up parameters. In some embodiments, controlling components of the stator 120 to achieve the operation/performance specified by the one or several back-up parameters can include generating one or several control signals that direct components of the stator to achieve the pump performance specified by the at least one back-up parameter.

After the blood pump operation/performance has been matched to the operation/performance specified by the one or several back-up parameters, the process 300 proceeds to block 322, wherein a new control signal is received. In some embodiments, the new control signal can be received from the system controller 20, and can be received when communication between the system controller 20 and the blood pump 100 is reestablished. In some embodiments, the new control signal can be received at any time. In some embodiments, the time between the control signal received in block 304 and the new control signal can be any time larger than the communication time. In some embodiments, this time between the control signal received in block 304 and the new control signal can be, for example, 1 second, 5 seconds, 10 seconds, 20 seconds, 30 seconds, 1 minute, 5 minutes, 10 minutes, 30 minutes, 1 hour, 1 day, 1 week, 1 month, 1 year, and/or any other or intermediate length of time. In some embodiments, the receipt of the new control signal can lead to the triggering of a return to normal status from the error and/or alarm state indicated in block 316. In some embodiments, a value can be associated with the restored normal state of operation, which value can be stored in the memory 206, and in some embodiments, in the RAM.

After the new control signal has been received, the process 300 proceeds to block 324, wherein the status response is provided. In some embodiments, the status response can be a response indicative of the status of the blood pump 100 that can be provided by the blood pump 100 to the system controller 20. In some embodiments, the status response can include information indicative of the current operation of the blood pump 100 including, for example, a speed, a mode, or a pulse parameter.

After the status response has been received, the process 300 proceeds to block 326, wherein the blood pump operation/performance is matched to the operation/performance specified by the new control signal. In some embodiments, this can include determining the current operation/performance of the blood pump 100, comparing the current operation/performance of the blood pump 100 to the operation/performance specified by the new control signal, and controlling components of the stator 120 to achieve the operation/performance specified by the new control signal if the current operation/performance of the blood pump 100 differs from the operation/performance specified by the new control signal. In some embodiments, the matching of the blood pump operation/performance to the operation/performance specified in the new control signal can further include the generation and transmission of a message by the control unit 202 to the system controller 20, which message can identify the current operation/performance of the blood pump 100.

Figure 11:
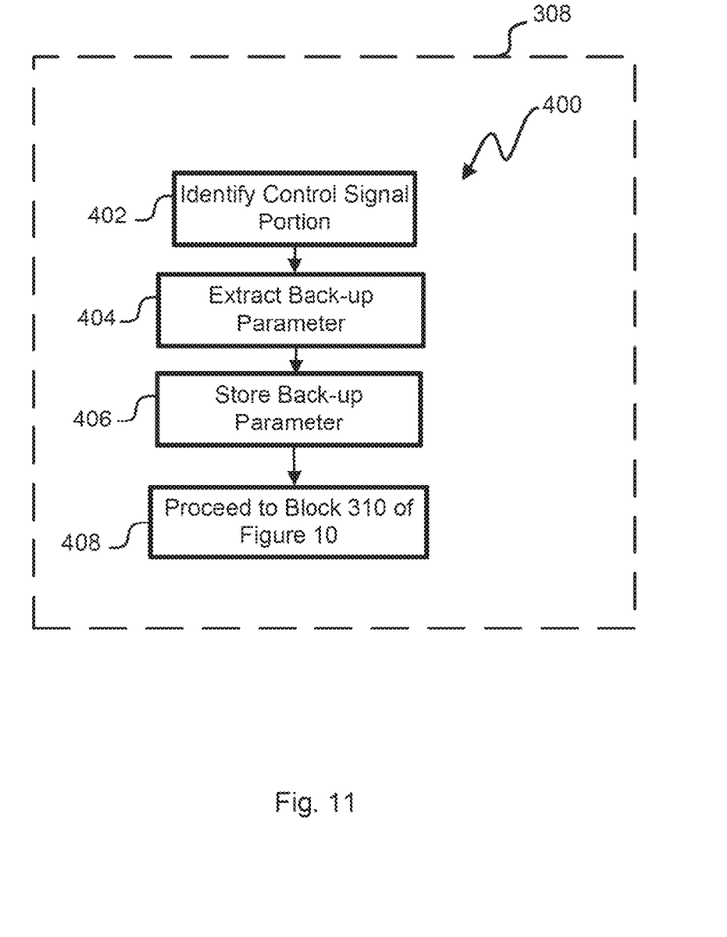
FIG. 11 is a flowchart illustrating one embodiment of process for generating a back-up parameter.

FIG. 11 is a flowchart illustrating one embodiment of process 400 for generating a back-up parameter. In some embodiments, the process 400 can be performed as part of block 308 shown in FIG. 10. The process 400 can be performed by the blood pump 100 and/or components thereof. The process begins at block 402, wherein control signal portions are identified. In some embodiments, the control signal can comprise one or several portions which can, in some embodiments, include unique information. In one embodiment, for example, the control signal can include a first portion that can include information relating to a speed of the blood pump 100, and a second portion that can include information relating to a mode of operation of the blood pump 100 and/or a pulse parameter of the blood pump 100. In one embodiment, the mode of operation of the blood pump 100 can specify pulsatile and/or non-pulsatile operation of the blood pump 100. In one embodiment, the pulse parameter can specify one of a pulse duration, a systolic pressure, a diastolic pressure, and/or a pulse pressure.

After the portions of the control signal have been identified, the process 400 proceeds to block 404 wherein the back-up parameter is extracted from, for example, the control signal. In some embodiments, the extraction of the back-up parameter can include the separation of one of the portions of the control signal from the other of the portions of the control signal. In one embodiment, the back-up parameter can comprise the first portion of the control signal, which first portion includes information relating to the speed of the blood pump 100.

After the back-up parameter has been extracted from the control signal, the process 400 proceeds to block 406, wherein the back-up parameter is stored. In some embodiments, the back-up parameter can be stored in the memory 206, including, for example, in the flash memory or in one of the partitions of the flash memory. After the back-up parameter has been stored, the process 400 proceeds to block 408 and continues with block 310 of FIG. 10.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of operating an implantable blood pump comprising a control unit, the method comprising:
  repeatedly receiving a control signal from a system controller with a control unit of the implantable blood pump, wherein the control signal comprises at least one blood pump performance parameter directing operation of the implantable blood pump;
  operating the blood pump with the control unit according to the control signal;
  triggering a threshold indicating absence of receipt of a new control signal from the system controller with the control unit;
  retrieving at least one back-up parameter from a memory in the control unit, wherein the at least one back-up parameter comprises a stored blood pump performance parameter; and
  operating the blood pump with the control unit according to the at least one back-up parameter.

2. The method of claim 1, wherein the at least one back-up parameter is retrieved from memory located on the blood pump.

3. The method of claim 1, wherein the threshold is triggered when a new control signal is not received within a predetermined time period.

4. The method of claim 3, wherein the predetermined time period comprises at least 5 seconds.

5. The method of claim 1, wherein the blood pump performance parameter comprises a first portion specifying a pump speed, and a second portion specifying a pulse parameter.

6. The method of claim 5, further comprising storing the first portion of the control signal as the at least one back-up parameter.

7. The method of claim 1, wherein when the blood pump is operating according to the at least one back-up parameter, receiving a second control signal, and operating the blood pump according to the second control signal.

* * * * *